US 8,675,046 B2

(12) United States Patent
Kubo et al.

(10) Patent No.: US 8,675,046 B2
(45) Date of Patent: Mar. 18, 2014

(54) ENDOSCOPE APPARATUS AND CONTROL METHOD THEREOF

(75) Inventors: Masahiro Kubo, Tokyo (JP); Makoto Kagaya, Tokyo (JP); Masayuki Takahira, Tokyo (JP); Masayuki Kuramoto, Tokyo (JP); Shuichi Ishii, Tokyo (JP); Ryo Takahashi, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 1034 days.

(21) Appl. No.: 12/633,559

(22) Filed: Dec. 8, 2009

(65) Prior Publication Data

US 2010/0141747 A1    Jun. 10, 2010

(30) Foreign Application Priority Data

Dec. 9, 2008    (JP) ................. 2008-313038

(51) Int. Cl.
*A61B 1/04* (2006.01)
(52) U.S. Cl.
USPC ............. 348/45; 348/42; 348/61; 348/65; 348/68
(58) Field of Classification Search
None
See application file for complete search history.

(56) References Cited

U.S. PATENT DOCUMENTS

| | | | | |
|---|---|---|---|---|
| 6,747,281 B2* | 6/2004 | Sendai et al. | ............... | 250/458.1 |
| 7,794,394 B2* | 9/2010 | Frangioni | ............... | 600/160 |
| 7,850,599 B2* | 12/2010 | Takeuchi et al. | ............... | 600/109 |
| 7,892,169 B2* | 2/2011 | Gono et al. | ............... | 600/178 |
| 2004/0046865 A1* | 3/2004 | Ueno et al. | ............... | 348/70 |
| 2006/0025692 A1* | 2/2006 | Ishihara | ............... | 600/478 |
| 2007/0183162 A1* | 8/2007 | Higuchi | ............... | 362/458 |
| 2009/0051764 A1* | 2/2009 | Ishii et al. | ............... | 348/68 |
| 2010/0127828 A1* | 5/2010 | Connolly et al. | ............... | 340/10.1 |

FOREIGN PATENT DOCUMENTS

| | | |
|---|---|---|
| EP | 1 177 761 A2 | 2/2002 |
| EP | 1 488 731 A1 | 12/2004 |
| EP | 1 757 221 A1 | 2/2007 |
| EP | 1 787 577 A1 | 5/2007 |
| EP | 1 992 275 A1 | 11/2008 |
| JP | 2003-93336 | 4/2003 |

OTHER PUBLICATIONS

European Search Report dated Apr. 23, 2010.

* cited by examiner

*Primary Examiner* — Joseph Ustaris
*Assistant Examiner* — William Adrovel
(74) *Attorney, Agent, or Firm* — McGinn IP Law Group, PLLC

(57) ABSTRACT

A narrow-band observation image and a spectral estimation image are automatically switched based on the type of a subject. In an endoscopic image obtained by a scope, judgment is made as to whether the endoscopic image was obtained by close-up imaging or by distant-view imaging. When it is judged that the endoscopic image was obtained by distant-view imaging, white light is output from a light source unit and a spectral estimation image is output. When it is judged that the endoscopic image was obtained by close-up imaging, narrow-band light is output from the light source unit and a narrow-band observation image that has been obtained when the narrow-band light was output is output.

9 Claims, 7 Drawing Sheets

FIG.3

| PARAMETER (WAVELENGTH) | $M_{j0}$ | $M_{j1}$ | $M_{j2}$ |
|---|---|---|---|
| p1 | 0.000083 | −0.00188 | 0.003592 |
| ⋮ | ⋮ | ⋮ | ⋮ |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| ⋮ | ⋮ | ⋮ | ⋮ |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −0.000036 |
| p51 | 0.005152 | −0.00192 | 0.000088 |
| p52 | 0.005215 | −0.00207 | 0.000217 |
| ⋮ | ⋮ | ⋮ | ⋮ |
| p61 | 0.00548 | −0.00229 | 0.00453 |

CLOSE-UP ENLARGEMENT MODE

DISTANT-VIEW MODE

ENDOSCOPE APPARATUS AND CONTROL METHOD THEREOF

BACKGROUND OF THE INVENTION

1. Field of the Invention

The present invention relates to an endoscope apparatus that controls various imaging modes and to a control method thereof.

2. Description of the Related Art

In recent years, in the field of electronic endoscope apparatuses using solid-state imaging devices, spectral imaging, in other words, electronic endoscope apparatuses with built-in narrow-band filters (Narrow Band Imaging—NBI) received attention. The Narrow Band Imaging uses narrow-band-pass filters in combination based on spectral reflectance in digestive organs (gastric mucosa (mucosa of stomach), or the like). In the NBI electronic endoscope apparatuses, three band-pass filters that pass light of narrow (wavelength) bands are provided instead of plane-sequential rotary filters of R (red), G (green), and B (blue). In the NBI electronic endoscope apparatuses, illumination light is sequentially output through the narrow-band-pass filters to obtain three signals. The three signals obtained by using the illumination light that has passed through the narrow-band-pass filters are processed in a manner similar to the processing on R, G and B signals (RGB signals), while weighting on each of the three signals is changed. Accordingly, spectral images are generated. When such spectral images are used, very fine structures in gasters (stomachs), large vowels (large intestines), or the like, which could not be observed (extracted) in conventional methods, are extracted.

Meanwhile, instead of the plane-sequential method using the narrow-band-pass filters, as described above, a method of forming spectral images by performing operation processing has been proposed (for example, please refer to Japanese Unexamined Patent Publication No. 2003-093336). The operation processing is performed based on image signals obtained by white light. Specifically, a relation between numerical value data representing the color sensitivity characteristic of each of R, G and B and numerical value data representing the spectral characteristic of specific narrow-band-pass filtered light is obtained as matrix data (coefficient sets). Further, spectral image signals that estimate spectral images obtained by passing light through the narrow-band-pass filter are estimated by performing operation on the matrix data and the RGB signals. When the spectral images are generated by performing such operations, it is not necessary to prepare a plurality of filters corresponding to wavelength bands that users need. Further, since it is not necessary to switchably arrange the filters, it is possible to prevent the size of the apparatuses (endoscope apparatuses or systems) from becoming large, and to reduce the cost of the apparatuses.

The characteristic of the narrow-band observation images obtained by illuminating subjects with narrow-band light and that of the spectral estimation images obtained by matrix operations, as described above, are not exactly the same. Therefore, the narrow-band observation images are suitable to observe some kinds of subjects, but the spectral estimation images are more suitable to observe some other kinds of subjects. Hence, it is desirable that the narrow-band observation images and the spectral estimation images are automatically switched, based on the subject, so that optimum images are displayed to observe the subjects.

SUMMARY OF THE INVENTION

In view of the foregoing circumstances, it is an object of the present invention to provide an endoscope apparatus that can automatically switch, based on the type of a subject, a narrow-band observation image and a spectral estimation image. Further, it is another object of the present invention to provide a method for controlling the endoscope apparatus.

An endoscope apparatus of the present invention is an endoscope apparatus comprising:

a light source unit that outputs white light and narrow-band light of a predetermined wavelength band to a subject;

a scope that obtains an endoscopic image by imaging the subject to which the white light or the narrow-band light has been output from the light source unit;

a spectral image generation means that generates a spectral estimation image by performing a matrix operation on the endoscopic image obtained by the scope when the white light was output to the subject;

an imaging state judgment means that judges whether the endoscopic image obtained by the scope has been obtained by close-up imaging or by distant-view imaging; and an imaging control means that controls imaging in such a manner that when the imaging state judgment means has judged that the endoscopic image was obtained by distant-view imaging, the white light is output from the light source unit and the spectral estimation image generated by the spectral image generation means is output, and when the imaging state judgment means has judged that the endoscopic image was obtained by close-up imaging, the narrow-band light is output from the light source unit and a narrow-band observation image that has been obtained when the narrow-band light was output is output.

A method for controlling an endoscope apparatus of the present invention is a method for controlling an endoscope apparatus that includes a light source unit that outputs white light and narrow-band light of a predetermined wavelength band to a subject, a scope that obtains an endoscopic image by imaging the subject to which the white light or the narrow-band light has been output from the light source unit, and a spectral image generation means that generates a spectral estimation image by performing a matrix operation on the endoscopic image obtained by the scope when the white light was output to the subject, the method comprising the steps of:

judging whether the endoscopic image obtained by the scope has been obtained by close-up imaging or by distant-view imaging; and when it is judged that the endoscopic image was obtained by distant-view imaging, outputting the white light from the light source unit and outputting the spectral estimation image generated by the spectral image generation means, and when it is judged that the endoscopic image was obtained by close-up imaging, outputting the narrow-band light from the light source unit and outputting a narrow-band observation image that has been obtained when the narrow-band light was output.

Here, the endoscopic image includes an ordinary observation image that is obtained when a subject is illuminated with white light and a narrow-band observation image that is obtained when the subject is illuminated with narrow-band light.

The imaging state judgment means should judge whether the endoscopic image has been obtained by close-up imaging or by distant-view imaging, and the method for judgment is not limited. For example, the light source unit may include a diaphragm (a mechanism for changing the amount of passing light) for adjusting the amount of light illuminating the subject. In this case, the imaging control means may have a function of automatically adjusting the diaphragm so that the brightness of the endoscopic image becomes a predetermined value. Further, the imaging state judgment means may judge, based on the aperture of the diaphragm (the degree of light passed by the diaphragm), whether the endoscopic image was obtained by close-up imaging or by distant-view imaging.

Alternatively, the light source unit may output light having a constant light amount (a fixed light amount) to the subject. In this case, the imaging state judgment means may judge, based on the brightness of the endoscopic image, whether the endoscopic image was obtained by close-up imaging or by distant-view imaging.

Further, the spectral image generation means may have a function of generating a spectral estimation image of the wavelength of 700 nm. In this case, the imaging state judgment means may judge, by using the spectral estimation image of the wavelength of 700 nm, whether the endoscopic image has been obtained by close-up imaging or by distant-view imaging.

According to the endoscope apparatus of the present invention and the method for controlling the endoscope apparatus of the present invention, the endoscope apparatus includes a light source unit that outputs white light and narrow-band light of a predetermined wavelength band to a subject, a scope that obtains an endoscopic image by imaging the subject to which the white light or the narrow-band light has been output from the light source unit, and a spectral image generation means that generates a spectral estimation image by performing a matrix operation on the endoscopic image obtained by the scope when the white light was output to the subject. Further, the method includes the steps of:

judging whether the endoscopic image obtained by the scope has been obtained by close-up imaging or by distant-view imaging; and when it is judged that the endoscopic image was obtained by distant-view imaging, outputting the white light from the light source unit and outputting the spectral estimation image generated by the spectral image generation means, and when it is judged that the endoscopic image was obtained by close-up imaging, outputting the narrow-band light from the light source unit and outputting a narrow-band observation image that has been obtained when the narrow-band light was output.

Therefore, when close-up imaging is performed, narrow-band observation images that can accurately (precisely) display very fine structures of the subject or the like are automatically obtained. In contrast, when distant-view imaging is performed, spectral estimation images are automatically obtained. The spectral estimation images can maintain the brightness of the images. Therefore, a change in the color tone (hue) of the subject is easily recognized by using the spectral estimation images. Hence, efficient diagnosis by using images is possible.

When the light source unit includes a diaphragm for adjusting the amount of light illuminating the subject, and the imaging control means has a function of automatically adjusting the diaphragm so that the brightness of the endoscopic image becomes a predetermined value, and the imaging state judgment means judges, based on the aperture of the diaphragm, whether the endoscopic image was obtained by close-up imaging or by distant-view imaging, it is possible to accurately judge whether imaging was performed by close-up imaging or by distant-view imaging.

When the light source unit outputs light having a constant light amount to the subject, and the imaging state judgment means judges, based on the brightness of the endoscopic image, whether the endoscopic image was obtained by close-up imaging or by distant-view imaging, it is possible to accurately judge whether imaging was performed by close-up imaging or by distant-view imaging.

Further, when the spectral image generation means has a function of generating a spectral estimation image of the wavelength of 700 nm, and the imaging state judgment means judges, by using the spectral estimation image of the wavelength of 700 nm, whether the endoscopic image has been obtained by close-up imaging or by distant-view imaging, it is possible to accurately judge, based on a spectral estimation image of near infrared light, whether imaging was performed by close-up imaging or by distant-view imaging. The rate of absorption of near infrared light by the subject is low.

BRIEF DESCRIPTION OF THE DRAWINGS

FIG. 3 is a table showing an example of matrix parameters used by a spectral image generation means illustrated in FIG. 1;

DESCRIPTION OF THE PREFERRED EMBODIMENTS

Figure 1:
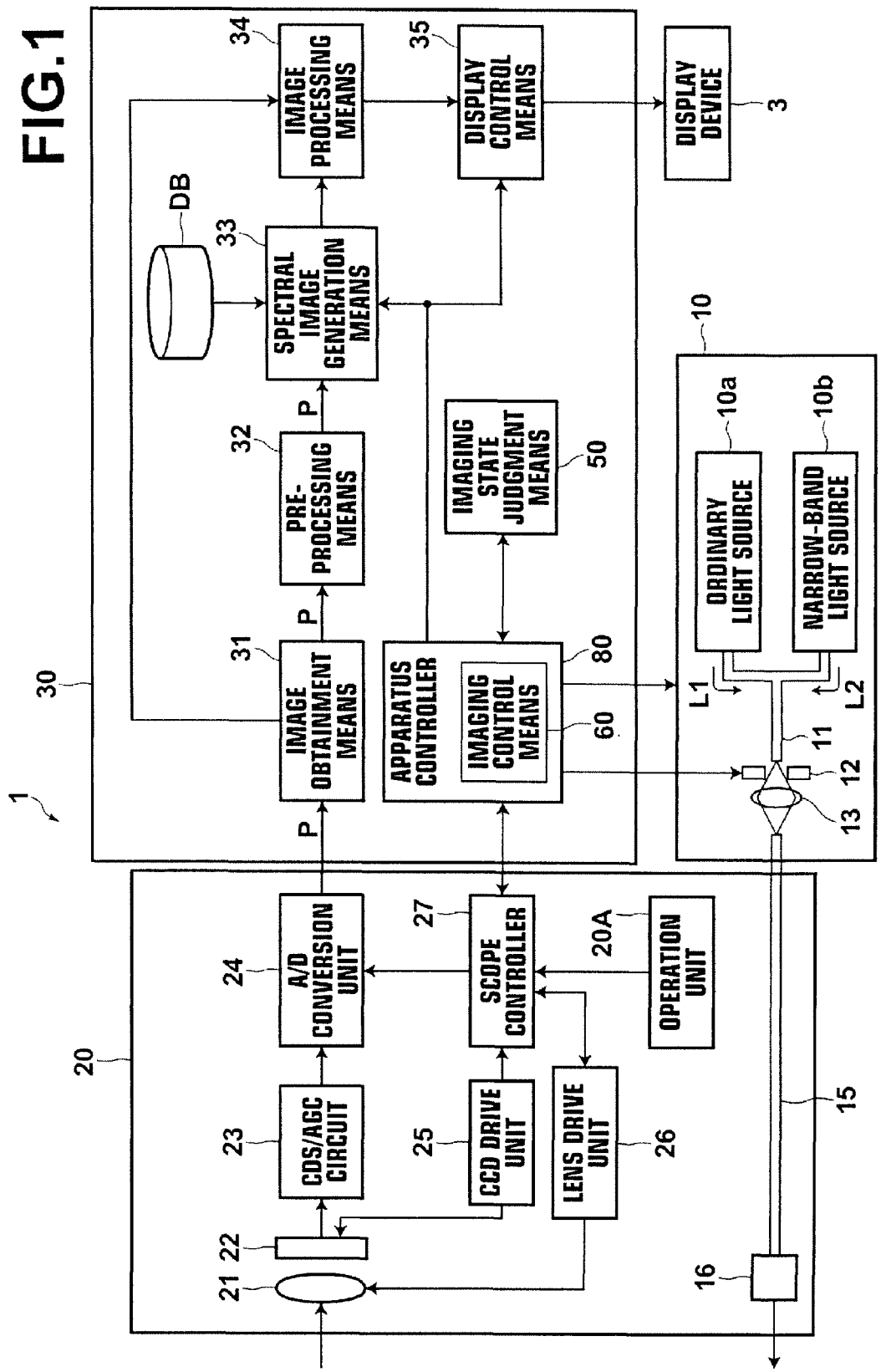
FIG. 1 is a block diagram illustrating an embodiment of an endoscope apparatus according to the present invention.
Figure 2:
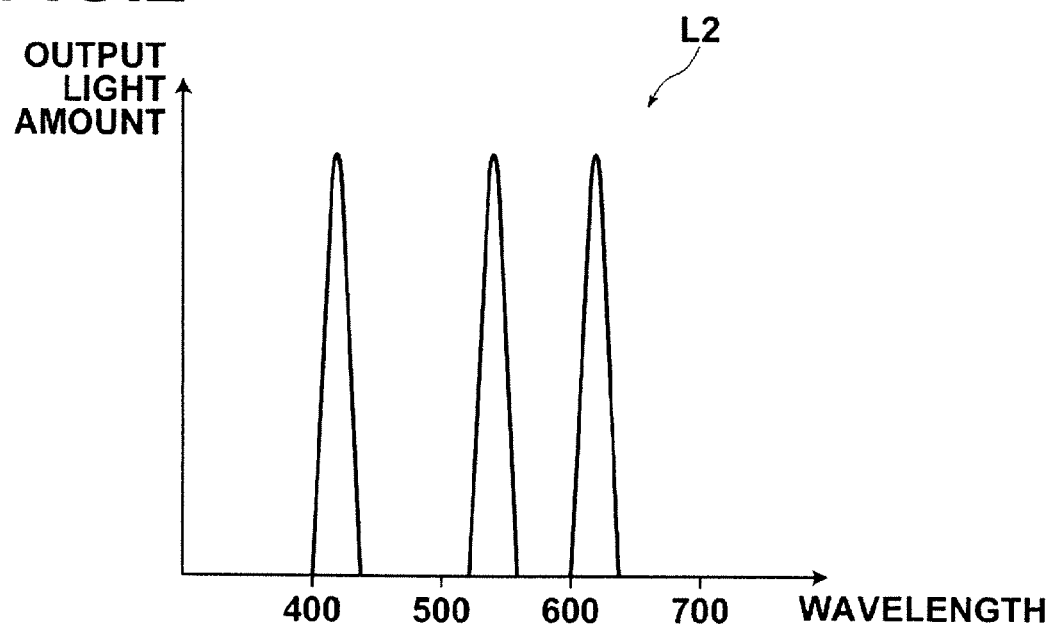
FIG. 2 is a graph showing an example of the spectrum of narrow-band light that is output from a light source unit illustrated in FIG. 1.

Hereinafter, embodiments of the present invention will be described with reference to drawings. FIG. 1 is a block diagram illustrating an example of an endoscope apparatus according to the present invention. An endoscope apparatus 1 includes a light source unit 10, a scope 20, and an image processing apparatus 30. The light source unit 10 outputs light to a subject to observe the subject by using an endoscope. The light source unit 10 includes an ordinary light source 10a, such as a xenon lamp, and a narrow-band light source 10b. The ordinary light source 10a outputs white light to perform ordinary observation, and the narrow-band light source 10b outputs narrow-band light. For example, the narrow-band light source 10b has a function of outputting narrow-wavelength-band light of the wavelength of 400 to 430 nm, narrow-wavelength-band light of the wavelength of 530 to 560 nm, and narrow-wavelength-band light of the wavelength of 600 to 630 nm, as illustrated in FIG. 2.

Each of the light sources 10a, 10b illustrated in FIG. 1 is optically connected to a light guide 15 of the scope 20 through an optical fiber 11 and a condensing lens 13. Therefore, white light L1 output from the ordinary light source 10a and narrow-band light L2 output from the narrow-band light source 10b enter the light guide 15, and are output from an observation window 16 to the subject. Further, the light source unit 10 has a diaphragm (an aperture diaphragm, a mechanism for changing the amount of passing light, or the like) 12. The diaphragm 12 adjusts the amount of light output from the observation window 16 to the subject. AEC (Auto Exposure Control) is performed on the diaphragm 12 by an imaging control means (controller) 60 so that the lightness (brightness) of endoscopic images P is maintained at a constant level. In FIG. 1, a case in which the light source unit 10 includes the ordinary light source 10a and the narrow-band light source 10b is illustrated. Alternatively, only the ordinary light source 10a may be provided, and narrow band light L2 may be output to the subject by use of an optical filter.

The scope 20 includes an imaging lens 21, an imaging means 22, a CDS/AGC (correlated double sampling/automatic gain control) circuit 23, an A/D (analog to digital) converter 24, a CCD (charge coupled device) drive unit 25, a lens drive unit 26, and the like. Further, each of these units is controlled by a scope controller 27. For example, the imaging lens 21 includes a set of a plurality of lenses, and the magnification of the imaging lens 21 is changed by driving the imaging lens 21 by the lens drive unit 26. The imaging means 22 includes a CCD, a CMOS (complementary metal oxide semiconductor) or the like, for example. The imaging means 22 obtains an image by performing photoelectric conversion on an image of a subject formed by the imaging lens 21. As the imaging means 22, a complementary-color type device or a primary-color type device may be used for example. The complementary-color type imaging means has color filters of Mg (magenta), Ye (yellow), Cy (cyan), and G (green) on the imaging surface. The primary-color type imaging means has color filters of RGB on the imaging surface. Further, the operation of the imaging means 22 is controlled by the CCD drive unit 25. When the imaging means 22 has obtained image (video) signals, the CDS/AGC (correlated double sampling/automatic gain control) circuit 23 performs sampling on the obtained signals, and amplifies the sampled signals. Further, the A/D converter 24 performs A/D conversion on an endoscopic image output from the CDS/AGC circuit 23, and outputs digital signals to the image processing apparatus 30.

The image processing apparatus 30 processes endoscopic images obtained by the scope 20. The image processing apparatus 30 is configured, for example, by DSP (digital signal processing) or the like. The image processing apparatus 30 includes an image obtainment means 31, a pre-processing means 32, a spectral image generation means 33, an image processing means 34, and a display control means 35. The image obtainment means 31 obtains endoscopic image P obtained by imaging by the imaging means 22 of the scope 20. The endoscopic image P obtained by the image obtainment means 31 includes ordinary observation image Pno, which is obtained when white light L1 is output to the subject, and narrow-band observation image Pnb, which is obtained when narrow-band light L2 is output to the subject.

The pre-processing means 32 performs pre-processing on the endoscopic image P obtained by the image obtainment means 31. For example, the pre-processing means 32 has a function of converting signals represented in a YCC color system to signals represented in an RGB color system when the endoscopic image P is represented by YCC color system. Further, the pre-processing means 32 has a gamma conversion function, a gradation adjustment function, and the like.

The spectral image generation means 33 generates spectral estimation image SP by performing matrix operation on the endoscopic image P by using matrix parameter M. An example of the operation by the spectral image generation means 33 is described, in detail, in Japanese Unexamined Patent Publication No. 2003-093336.

Specifically, the spectral image generation means 33 generates the spectral estimation image SP by performing matrix operation represented by the following equation (1):

$$\begin{pmatrix} SP_r \\ SP_g \\ SP_b \end{pmatrix} = \begin{pmatrix} M_{00} & M_{01} & M_{02} \\ M_{10} & M_{11} & M_{12} \\ M_{20} & M_{21} & M_{22} \end{pmatrix} \cdot \begin{pmatrix} Pr \\ Pg \\ Pb \end{pmatrix}. \quad (1)$$

In the equation (1), $SP_r$, $SP_g$, and $SP_b$ represent RGB components of the spectral estimation image SP, respectively. Pr, Pg, and Pb represent RGB components of the endoscopic image P, respectively. A matrix of 3×3 including $M_{00}$ to $M_{22}$ represents matrix parameters M for performing the matrix operation.

For example, as illustrated in FIG. 3, database DB stores matrix parameters $pi=(M_{j0}, M_{j1}, M_{j2})$ (i=1 to 61, j is the row of matrix parameter M, and j=0 to 2). For example, the wavelength range of from 400 nm to 700 nm is divided into wavelength bands of 5 nm, and the matrix parameter is stored for each wavelength band of 5 nm. For example, when 500 nm, 620 nm, and 650 nm are selected as wavelength bands λ1, λ2, λ3, which constitute the spectral estimation image SP, the matrix operation is performed by using, as coefficients ($M_{j0}$, $M_{j1}$, $M_{j2}$), coefficients of three parameters selected from 61 parameters in the table illustrated in FIG. 3. Specifically, coefficients (−0.00119, 0.002346, 0.0016) of parameter p21, which corresponds to the center wavelength of 500 nm, coefficients (0.004022, 0.000068, −0.00097) of parameter p45, which corresponds to the center wavelength of 620 nm, and coefficients (0.005152, −0.00192, 0.000088) of parameter p51, which corresponds to the center wavelength of 650 nm, are used to perform the matrix operation.

The combination of the parameters as described above is stored in the database DB for each region to be observed, such as blood vessels and tissue of a living body. The spectral estimation image SP is generated by using parameters that match each region of the body. For example, eight wavelength sets for setting the matrix parameters M are stored in the database DB. The eight wavelength sets are, for example, standard set CH1, blood-vessel sets CH2, CH3 for drawing blood vessels, tissue sets CH4, CH5 for drawing specific tissue, hemoglobin set CH6 for drawing a difference between oxyhemoglobin and deoxyhemoglobin, blood-carotene set CH7 for drawing a difference between blood and carotene, and blood-cytoplasm set CH8 for drawing a difference between blood and cytoplasm. The standard set CH1 is, for example, (λ1, λ2, λ3)=(400, 500, 600). The blood-vessel sets CH2, CH3 are, for example, (λ1, λ2, λ3)=(470, 500, 670) and (λ1, λ2, λ3)=(475, 510, 685), respectively. The tissue sets CH4, CH5 are, for example, (λ1, λ2, λ3)=(440, 480, 520) and (λ1, λ2, λ3)=(480, 510, 580), respectively. The hemoglobin set CH6 is, for example, (λ1, λ2, λ3)=(400, 430, 475). The blood-carotene set CH7 is, for example, (λ1, λ2, λ3)=(415, 450, 500). The blood-cytoplasm set CH8 is, for example, (λ1, λ2, λ3)=(420, 550, 600).

The image processing means 34 illustrated in FIG. 1 performs enhancement processing or the like on the endoscopic image P and the spectral estimation images SP. The display control means 35 has a function of displaying the endoscopic image P and the spectral estimation image SP that have been processed by the image processing means 34 on the display device 3 together with character information or the like. Specifically, the display control means 35 has a function of displaying, as the endoscope images, the ordinary observation image obtained when the white light L1 is output and the narrow-band observation image obtained when the narrow-band light L2 is output.

Figure 4:
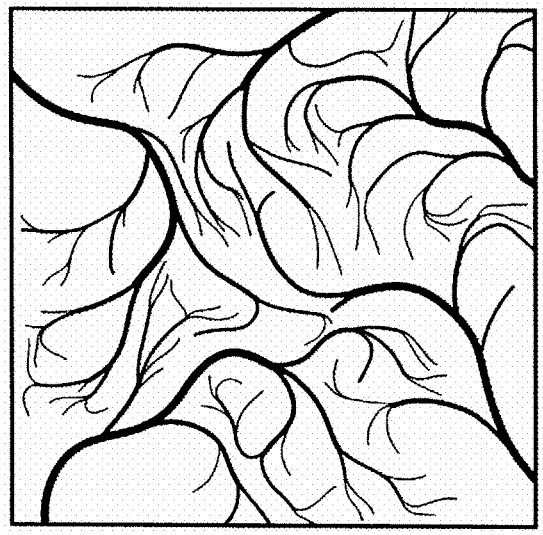
FIG. 4 is a schematic diagram illustrating an example of an endoscopic image obtained by performing close-up imaging in the endoscope apparatus illustrated in FIG. 1.
Figure 5:
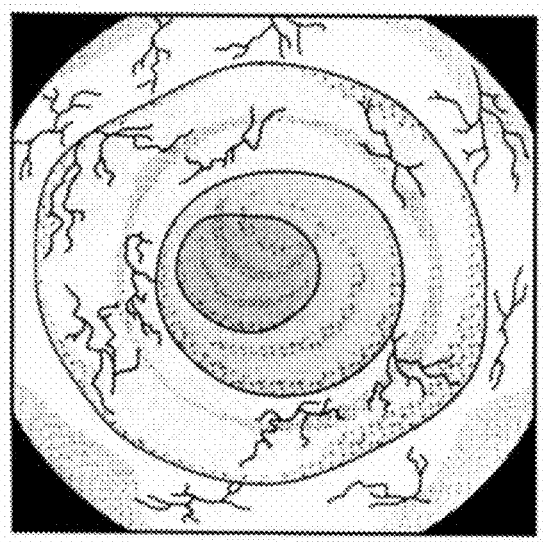
FIG. 5 is a schematic diagram illustrating an example of an endoscopic image obtained by performing distant-view imaging in the endoscope apparatus illustrated in FIG. 1.

The imaging state judgment means 50 judges whether the endoscopic image P was obtained by close-up imaging or by distant-view imaging. The term "close-up imaging" means imaging performed in a state in which the subject and the leading end of the scope 20 or a hood (cover) attached to the leading end of the scope 20 are in contact with each other, or only slightly away from each other (they are not in contact with each other, but away from each other only by a small distance). In close-up imaging, for example, an uneven pattern on the surface of the subject and fine blood vessels, as illustrated in FIG. 4, appear on the obtained images. In contrast, the term "distant-view imaging" means imaging performed when the leading end of the scope and the subject are away from each other. In distant-view imaging, for example, the shape of the entire area of the subject and relatively thick blood vessels, or the like, as illustrated in FIG. 5, appear on the obtained images.

Here, the imaging state judgment means 50 detects a distance from the scope 20 to the subject based on the aperture (the degree of passing or blocking light by the diaphragm) of the diaphragm 12 in the light source unit 10. Further, the imaging state judgment means 50 judges, based on the detection result, whether imaging was performed by close-up imaging or by distant-view imaging. Specifically, when the distance between the leading end of the scope 20 and the subject is long, the amount of light (reflection light) that is reflected from the subject and enters the imaging means 22 is small. Therefore, the degree of closing the aperture of the diaphragm 12 on which AEC control is performed to maintain the brightness at a constant level is small (the aperture of the diaphragm 12 is large). In contrast, when the distance between the leading end of the scope 20 and the subject is small, the amount of light (reflection light) that is reflected from the subject and enters the imaging means 22 is large. Therefore, the degree of closing the aperture of the diaphragm 12 on which AEC control is performed to maintain the brightness at a constant level is large (the aperture of the diaphragm 12 is small). When the degree of closing the aperture of the diaphragm 12 is greater than or equal to a predetermined threshold value, the imaging state judgment means 50 judges that imaging has been performed by close-up imaging. When the degree of closing the aperture of the diaphragm 12 is less than the predetermined threshold value, the imaging state judgment means 50 judges that imaging has been performed by distant-view imaging.

The imaging control means 60 illustrated in FIG. 1 automatically switches the imaging condition based on the imaging state judged by the imaging state judgment means 50. Specifically, when the imaging state judgment means 50 judges that imaging has been performed by close-up imaging, the imaging control means 60 controls the light source unit 10 so that narrow-band light L2 is output to the subject. Further, the imaging control means 60 controls the display control means 35 so that narrow-band observation image Pnb obtained when the narrow-band light L2 was output is displayed. In contrast, when the imaging state judgment means 50 judges that imaging has been performed by distant-view imaging, the imaging control means 60 controls the light source unit 10 so that white light L1 is output to the subject. Further, the spectral image generation means 33 generates spectral estimation image SP by using a predetermined wavelength set, and the display control means 35 controls to display the spectral estimation image SP.

As described above, when imaging has been performed by close-up imaging, the narrow-band observation image Pnb is obtained and displayed. When imaging has been performed by distant-view imaging, the spectral estimation image SP is obtained and displayed. Therefore, it is possible to utilize the advantage of each observation mode and to perform efficient diagnosis by using images (image diagnosis). Specifically, in close-up imaging, it is desirable that the surface of the subject or a fine structure in a surface layer of the subject clearly appears in images. In close-up imaging, since the leading end of the scope 20 and the subject are close to each other, the amount of light is always sufficient. In contrast, in distant-view imaging, it is necessary to identify a region of the subject at which the color tone (hue) changes. Further, in distant-view imaging, since the leading end of the scope 20 and the subject are away from each other, a predetermined amount of light is necessary. Therefore, in close-up imaging, the narrow-band observation image Pnb is output, and in distant-view imaging, the spectral estimation image SP is output. In the narrow-band observation image Pnb, it is impossible to increase the light amount, but a fine structure on the surface (surface layer) of the subject clearly appears. In contrast, in the spectral estimation image SP, a change in the color tone (hue) is easily identified (observed), and the spectral estimation image SP can be obtained by illuminating the subject with a predetermined amount of light. Hence, it is possible to automatically display optimum images for each region to be observed.

Figure 6:
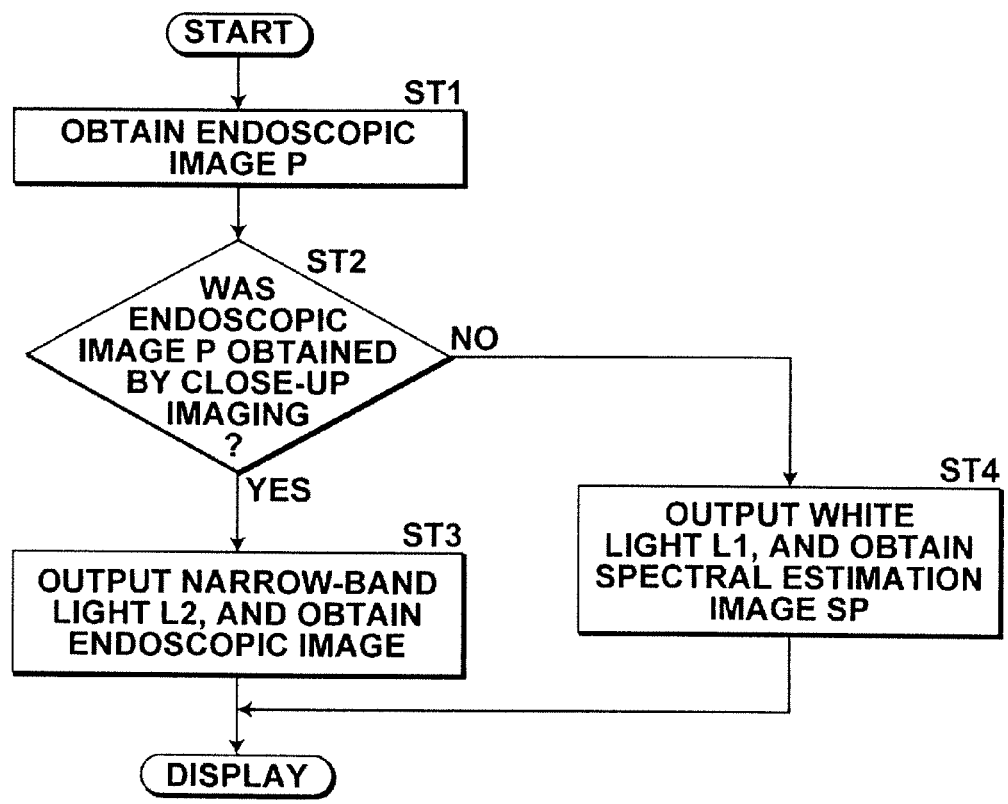
FIG. 6 is a flow chart illustrating an embodiment of an endoscopic image processing method of the present invention.

FIG. 6 is a flow chart illustrating an embodiment of an endoscopic image processing method of the present invention. With reference to FIGS. 1 through 6, the endoscopic image processing method will be described. First, imaging is performed while the scope 20 is inserted into the body cavity of a patient. Accordingly, an endoscopic image P is obtained (step ST1). At this time, judgment is made, based on the aperture of the diaphragm of the light source unit 10, as to whether imaging has been performed by close-up imaging or by distant-view imaging (step ST2). When the imaging state judgment means 50 judges that imaging has been performed by close-up imaging, the imaging control means 60 sets the imaging mode to close-up enlargement mode. Further, narrow-band light L2 is output to the subject, and narrow-band observation image Pnb is obtained and displayed (step ST3).

In contrast, when the imaging state judgment means 50 judges that imaging has been performed by distant-view imaging, the imaging control means 60 sets the imaging mode to distant-view mode. Further, white light L1 is output to the subject, and spectral estimation image SP is obtained by the spectral estimation means 33, and displayed (step ST4). As described above, when imaging is performed by close-up imaging, the narrow-band observation image Pnb is obtained and displayed. When imaging is performed by distant-view imaging, the spectral estimation image SP is obtained and displayed. Therefore, it is possible to utilize the advantage of each observation mode, and to perform efficient diagnosis by using images.

Figure 7:
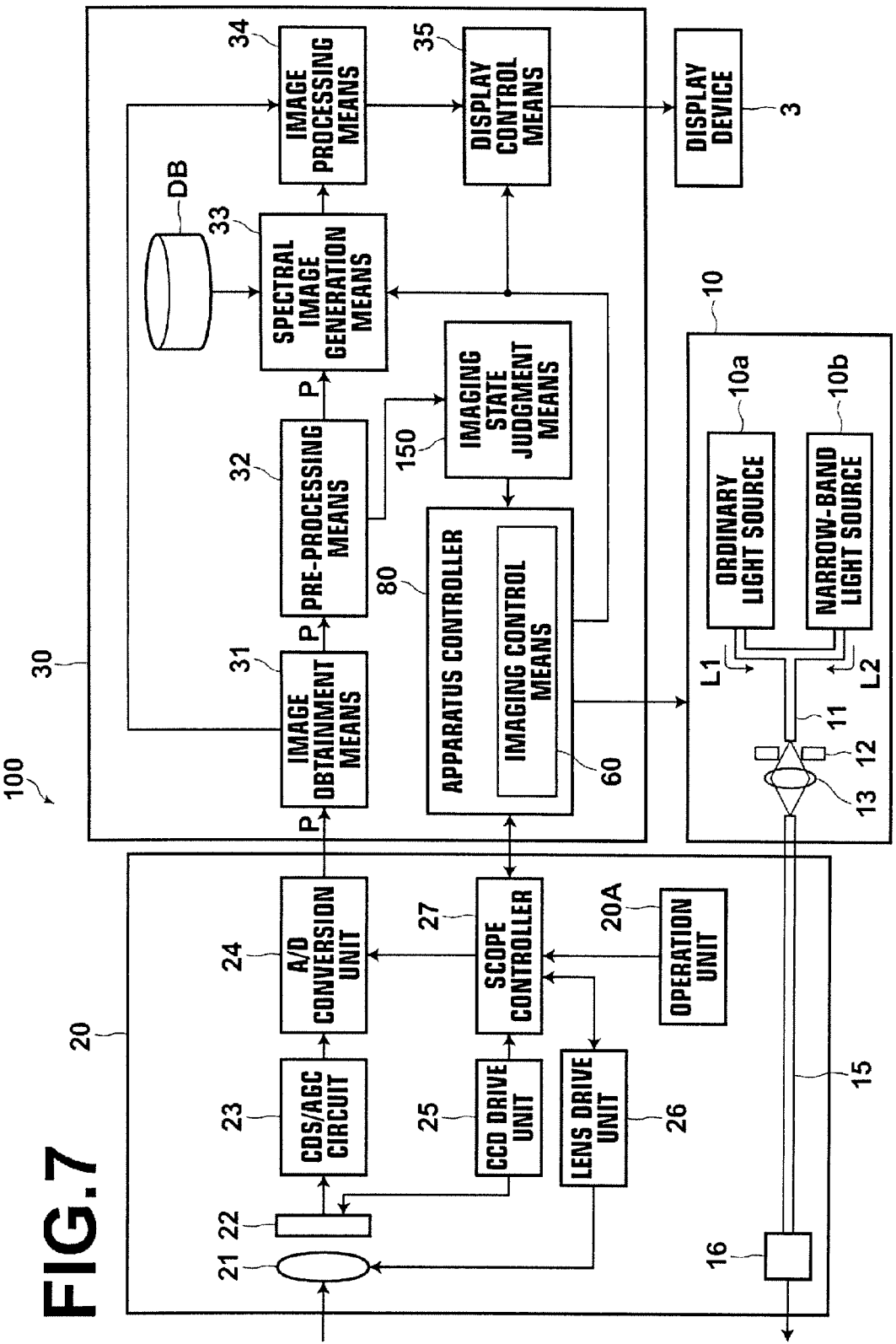
FIG. 7 is a block diagram illustrating a second embodiment of an endoscope apparatus of the present invention.

FIG. 7 is a block diagram illustrating a second embodiment of an endoscope apparatus of the present invention. With reference to FIG. 7, an endoscope apparatus 100 will be described. In the endoscope apparatus 100 illustrated in FIG. 7, the same reference numerals will be assigned to elements or units corresponding to those of the endoscope apparatus 1 illustrated in FIG. 1, and the explanation thereof will be omitted. The endoscope apparatus 100 illustrated in FIG. 7 differs from the endoscope apparatus 1 illustrated in FIG. 1 in that the endoscope apparatus 100 judges, based on the brightness of ordinary observation image Pno, whether imaging has been performed by close-up imaging or by distant-view imaging.

Specifically, in FIG. 7, the light source unit 10 is controlled to output white light L1 at a constant light amount. Therefore, the brightness of the ordinary observation image Pno increases as the scope 20 becomes closer to the subject. The brightness of the ordinary observation image Pno decreases as the scope 20 becomes away from the subject. Therefore, an imaging state judgment means 150 judges, based on the brightness of the ordinary observation image Pno, whether imaging has been performed by close-up imaging or by distant-view imaging. Specifically, when the brightness of the ordinary observation image Pno is greater than or equal to a threshold value, the imaging state judgment means 150 judges that imaging has been performed by close-up imaging. When the brightness of the ordinary observation image Pno is less than the threshold value, the imaging state judgment means 150 judges that imaging has been performed by distant-view imaging. Like the aforementioned embodiment, it is possible to accurately judge the imaging state and to perform efficient diagnosis by using images.

Figure 8:
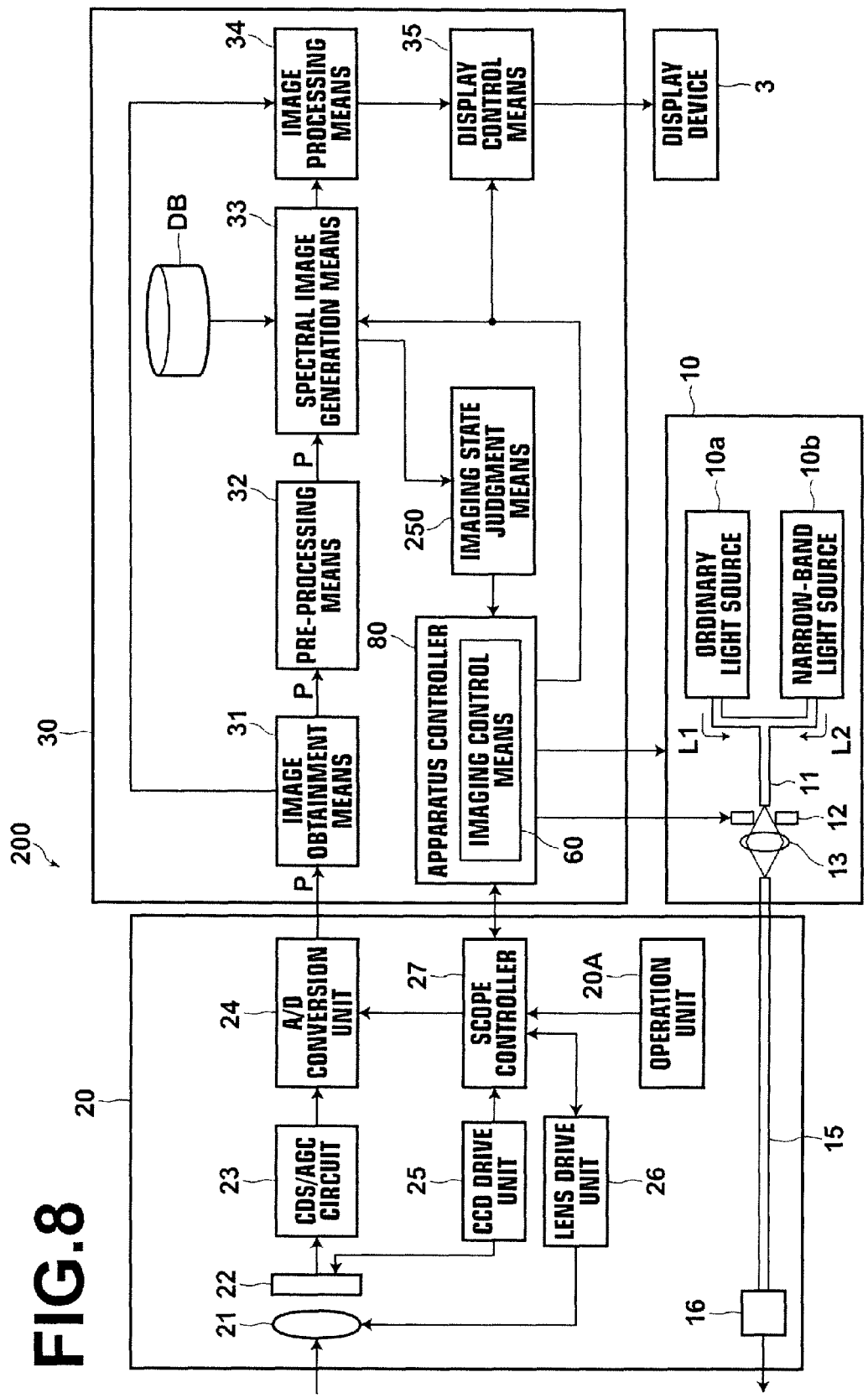
FIG. 8 is a block diagram illustrating a third embodiment of an endoscope apparatus of the present invention.

FIG. 8 is a block diagram illustrating a third embodiment of an endoscope apparatus of the present invention. With reference to FIG. 8, an endoscope apparatus 200 will be described. In the endoscope apparatus 200 illustrated in FIG. 8, the same reference numerals will be assigned to elements or units corresponding to those of the endoscope apparatus 1 illustrated in FIG. 1, and the explanation thereof will be omitted. The endoscope apparatus 200 illustrated in FIG. 8 differs from the endoscope apparatus 1 illustrated in FIG. 1 in that the endoscope apparatus 200 judges, by using spectral estimation image SP of the wavelength of 700 nm, whether imaging has been performed by close-up imaging or by distant-view imaging.

Specifically, the spectral image generation means 33 has a function of generating spectral estimation image SP for judging whether imaging has been performed by close-up imaging or by distant-view imaging. For example, the spectral image generation means 33 generates spectral estimation image SP of the wavelength of 700 nm. Further, an imaging state judgment means 250 judges, by using the spectral estimation image SP of the wavelength of 700 nm, whether imaging has been performed by close-up imaging or by distant-view imaging. Specifically, the imaging state judgment means 250 judges that imaging has been performed by close-up imaging when an average value of pixel values (brightness values) of the spectral estimation image SP of the wavelength of 700 nm, or the number of pixels having values greater than or equal to a predetermined value, or the like is greater than or equal to a threshold value. When the average value of pixel values (brightness values) of the spectral estimation image SP of the wavelength of 700 nm, or the number of pixels having values greater than or equal to a predetermined value, or the like is less than a threshold value, the imaging state judgment means 250 judges that imaging has been performed by distant-view imaging. As described above, spectral estimation images of near-infrared light, in which the rate of absorption by living tissue is low, are used. Therefore, the brightness values reflect the distance to the subject, and it is possible to accurately judge the imaging state.

According to the aforementioned embodiments, the endoscope apparatus includes the light source unit 10, the scope 20, and the spectral image generation means 33. The light source unit 10 outputs white light L1 and narrow-band light L2 of a predetermined wavelength band to a subject. The scope 20 obtains endoscopic image P by imaging the subject illuminated with light output from the light source unit 10. The spectral image generation means 33 generates spectral estimation image SP by performing a matrix operation on the endoscopic image obtained by the scope 20 when the subject was illuminated with white light L1. Further, judgment is made on the endoscopic image P obtained by the scope 20 as to whether the endoscopic image has been obtained by performing close-up imaging on the subject or by performing distant-view imaging on the subject. When it is judged that the endoscopic image has been obtained by distant-view imaging, the light source unit 10 outputs the white light L1, and the spectral image generation means 33 generates and outputs spectral estimation image SP. When it is judged that the endoscopic image has been obtained by close-up imaging, the light source unit 10 outputs narrow-band light L2, and operation is controlled so that narrow-band observation image Pnb obtained when the subject was illuminated with the narrow-band light L2 is output. Therefore, in close-up imaging, the narrow-band observation image Pnb, which can accurately display fine structures of the subject or the like, is automatically obtained. In distant-view imaging, the spectral estimation image SP, which can maintain the brightness of the image, and in which a change in the light tone (hue) of the subject is easily identified, is automatically obtained. Therefore, efficient diagnosis by using images is possible.

When the light source unit 10 includes a diaphragm for adjusting the amount of light illuminating the subject, and the imaging control means 60 has a function of automatically adjusting the diaphragm (aperture) so that the brightness of the endoscopic image P becomes a predetermined value, and the imaging state judgment means 50 judges, based on the aperture of the diaphragm, whether imaging has been performed by close-up imaging or by distant-view imaging, it is possible to accurately judge whether imaging has been performed by close-up imaging or by distant-view imaging.

Further, when the light source unit 10 illuminates the subject with light of a constant light amount, and the imaging state judgment means 50 judges, based on the brightness of the endoscopic image P, whether imaging has been performed by close-up imaging or by distant-view imaging, it is possible to accurately judge whether imaging has been performed by close-up imaging or by distant-view imaging.

Further, when the spectral image generation means 33 has a function of generating a spectral estimation image of the wavelength of 700 nm, and the imaging state judgment means 50 judges, by using the spectral estimation image of the wavelength of 700 nm, whether imaging has been performed by close-up imaging or by distant-view imaging, it is possible to accurately judge, based on the spectral estimation image SP of near-infrared light, whether imaging has been performed by close-up imaging or by distant-view imaging. In the near-infrared region, the ratio of absorption by living tissue is small.

What is claimed is:

1. An endoscope apparatus, comprising:
a light source unit that outputs white light and narrow-band light of a predetermined wavelength band to a subject;
a scope that obtains an endoscopic image by imaging the subject to which the white light or the narrow-band light has been output from the light source unit;
spectral image generation means that generates a spectral estimation image by performing a matrix operation on the endoscopic image obtained by the scope when the white light was output to the subject;
imaging state judgment means that judges whether the endoscopic image obtained by the scope has been obtained by a close-up imaging or by a distant-view imaging; and
imaging control means that controls imaging in such a manner that when the imaging state judgment means has judged that the endoscopic image was obtained by the distant-view imaging, the white light is output from the light source unit and the spectral estimation image generated by the spectral image generation means is output, and when the imaging state judgment means has judged that the endoscopic image was obtained by the close-up imaging, the narrow-band light is output from the light source unit and a narrow-band observation image that has been obtained when the narrow-band light was output is output, wherein the light source unit includes a diaphragm for adjusting an amount of light illuminating the subject, wherein the imaging control means comprises a function of automatically adjusting the diaphragm, without a user interaction, so that a brightness of the endoscopic image becomes a predetermined value, and wherein the imaging state judgment means judges, based on the aperture of the diaphragm, whether the endoscopic image was obtained by the close-up imaging or by the distant-view imaging.

2. An endoscope apparatus, as defined in claim 1, wherein the close-up imaging is distinguished from the distant-view imaging based on a distance between the subject and a leading end of the scope.

3. An endoscope apparatus, as defined in claim 1, wherein the distant-view imaging is applied when a leading end of the scope is placed farther than a predetermined distance from the subject, and the close-up imaging is applied when the leading end of the scope is placed closer than the predetermined distance from the subject.

4. An endoscope apparatus, as defined in claim 1, wherein an imaging format is determined after an amount of an opening of the diaphragm and the brightness of endoscopic image are determined.

5. An endoscope apparatus, as defined in claim 1, wherein the spectral image generation means comprises a function of generating a spectral estimation image.

6. A method for controlling an endoscope apparatus that includes a light source unit that outputs white light and narrow-band light of a predetermined wavelength band to a subject, a scope that obtains an endoscopic image by imaging the subject to which the white light or the narrow-band light has been output from the light source unit, and spectral image generation means that generates a spectral estimation image by performing a matrix operation on the endoscopic image obtained by the scope when the white light was output to the subject, the method comprising:

judging whether the endoscopic image obtained by the scope has been obtained by a close-up imaging or by a distant-view imaging; and when it is judged that the endoscopic image was obtained by the distant-view imaging, outputting the white light from the light source unit and outputting the spectral estimation image generated by the spectral image generation means, and when it is judged that the endoscopic image was obtained by the close-up imaging, outputting the narrow-band light from the light source unit and outputting a narrow-band observation image obtained when the narrow-band light was output, wherein the light source unit includes a diaphragm for adjusting an amount of light illuminating the subject, wherein the judging that the endoscopic image was obtained by the distant-view imaging includes a function of automatically adjusting the diaphragm, without a user interaction, so that a brightness of the endoscopic image becomes a predetermined value, and wherein, based on the aperture of the diaphragm, it is judged whether the endoscopic image was obtained by the close-up imaging or by the distant-view imaging.

7. The method of claim 6, wherein the close-up imaging is distinguished from the distant-view imaging based on a distance between the subject and a leading end of the scope.

8. The method of claim 6, wherein the distant-view imaging is applied when a leading end of the scope is placed farther than a predetermined distance from the subject, and the close-up imaging is applied when the leading end of the scope is placed closer than the predetermined distance from the subject.

9. The method of claim 6, wherein the spectral image generation means comprises a function of generating a spectral estimation image.

* * * * *